(12) United States Patent
Guan et al.

(10) Patent No.: US 10,463,243 B2
(45) Date of Patent: Nov. 5, 2019

(54) STRUCTURED LIGHT GENERATION FOR INTRAORAL 3D CAMERA USING 1D MEMS SCANNING

(71) Applicant: Carestream Dental Technology Topco Limited, London (GB)

(72) Inventors: Yiyi Guan, Pittsford, NY (US); Victor C. Wong, Rochester, NY (US); Chuanmao Fan, Rochester, NY (US)

(73) Assignee: CARESTREAM DENTAL TECHNOLOGY TOPCO LIMITED, London (GB)

( * ) Notice: Subject to any disclaimer, the term of this patent is extended or adjusted under 35 U.S.C. 154(b) by 133 days.

(21) Appl. No.: 15/460,760

(22) Filed: Mar. 16, 2017

(65) Prior Publication Data

US 2018/0263482 A1 Sep. 20, 2018

(51) Int. Cl.
*A61B 1/24* (2006.01)
*F21V 14/04* (2006.01)
(Continued)

(52) U.S. Cl.
CPC ............ *A61B 1/24* (2013.01); *A61B 1/00006* (2013.01); *A61B 1/00172* (2013.01);
(Continued)

(58) Field of Classification Search
CPC ....... A61B 1/24; A61B 1/045; A61B 1/00172; A61B 1/063; A61B 1/055; A61B 1/00006;
(Continued)

(56) References Cited

U.S. PATENT DOCUMENTS 5,372,502 A 12/1994 Massen et al.
6,201,880 B1 * 3/2001 Elbaum .................... A61B 1/24
348/66
(Continued)

FOREIGN PATENT DOCUMENTS

CN 102613954 8/2012
WO WO 2010/096634 8/2010
(Continued)

OTHER PUBLICATIONS

Aoki, Hiroshi, "Development of portable 3D optical measuring system using structured light projection method," Proc. SPIE 9110, Dimensional Optical Metrology and Inspection for Practical Applications III, 91100Q1-8 (May 28, 2014) (Year: 2014).*
(Continued)

*Primary Examiner* — James M Pontius

(57) ABSTRACT

An apparatus for intraoral imaging has an intraoral camera that defines a field of view with a first dimension and a second dimension orthogonal to the first dimension. A projector has a laser diode energizable to emit a light beam; a collimator in the path of the emitted light beam; first beam-shaping optics disposed to shape the collimated light beam in the second dimension to form a linear light pattern; focusing optics disposed to focus the shaped collimated beam at a focal plane; and a scanner that is disposed substantially at the focal plane and that is energizable to scan the formed linear light pattern along the second dimension to successive positions of the field of view. A control logic processor coordinates energizing the laser diode and scanner with image capture by the intraoral camera.

20 Claims, 8 Drawing Sheets

(51) Int. Cl.

| | |
|---|---|
| *F21V 13/06* | (2006.01) |
| *F21V 5/04* | (2006.01) |
| *G02B 27/09* | (2006.01) |
| *A61B 1/00* | (2006.01) |
| *A61B 1/055* | (2006.01) |
| *A61B 1/06* | (2006.01) |
| *H04N 13/254* | (2018.01) |
| *H04N 13/296* | (2018.01) |
| *A61B 1/045* | (2006.01) |
| *G02B 26/10* | (2006.01) |
| *G02B 27/30* | (2006.01) |
| *F21Y 115/30* | (2016.01) |

(52) U.S. Cl.
CPC ............. *A61B 1/045* (2013.01); *A61B 1/055* (2013.01); *A61B 1/063* (2013.01); *F21V 5/043* (2013.01); *F21V 13/06* (2013.01); *F21V 14/04* (2013.01); *G02B 26/105* (2013.01); *G02B 27/0927* (2013.01); *G02B 27/0966* (2013.01); *G02B 27/30* (2013.01); *H04N 13/254* (2018.05); *H04N 13/296* (2018.05); *F21Y 2115/30* (2016.08); *H04N 2213/001* (2013.01)

(58) Field of Classification Search
CPC .. G02B 27/30; G02B 26/105; G02B 27/0966; G02B 27/0927; F21V 5/043; F21V 13/06; F21V 14/04; F21Y 2115/30; H04N 2213/001; H04N 13/296; H04N 13/254
See application file for complete search history.

(56) References Cited

U.S. PATENT DOCUMENTS

| | | | |
|---|---|---|---|
| 6,885,464 B1 | 4/2005 | Pfeiffer et al. | |
| 7,312,924 B2 | 12/2007 | Trissel | |
| 2005/0100333 A1* | 5/2005 | Kerschbaumer | A61B 1/0676 396/16 |
| 2005/0190988 A1 | 9/2005 | Feron | |
| 2007/0086762 A1 | 4/2007 | O'Keefe et al. | |
| 2010/0268069 A1 | 10/2010 | Liang | |
| 2012/0322025 A1* | 12/2012 | Ozawa | A61C 9/0053 433/29 |
| 2013/0120532 A1 | 5/2013 | Milch | |
| 2013/0120533 A1 | 5/2013 | Milch | |
| 2013/0169974 A1* | 7/2013 | Iwayama | B29D 30/3007 356/601 |
| 2014/0176959 A1* | 6/2014 | Liu | G01B 9/0209 356/479 |

FOREIGN PATENT DOCUMENTS

| | | |
|---|---|---|
| WO | WO 2010/145669 | 12/2010 |
| WO | WO 2011/145799 | 11/2011 |
| WO | WO 2016/041147 | 3/2016 |

OTHER PUBLICATIONS

International Search Report dated Jun. 19, 2015 for International Application No. PCT/CN2014/086635, 2 pages.

Y. Takaki, "Micromirrors and 1D Scanning Produce an Enlarged Holographic Color Display", SPIE, 2014, pp. 1-3.

H. Aoki et al., "Development of Portable 3D Optical Measuring System Using Structured Light Projection Method", Proceedings of SPIE, vol. 9110, 2014, pp. 91100Q-1-91100Q-8.

T. Wakayama et al., "Compact Camera for Real-Time 3D Measurement", 10th IMEKO TC14 Symposium on Laser Metrology for Precision Measurement and Inspection in Industry, Sep. 2011, pp. 1-6.

* cited by examiner

STRUCTURED LIGHT GENERATION FOR INTRAORAL 3D CAMERA USING 1D MEMS SCANNING

TECHNICAL FIELD

The disclosure relates generally to the field of intraoral imaging and more particularly relates to a method for generating structured light image content to enable surface characterization of teeth and other intraoral features.

BACKGROUND

Surface contour imaging uses patterned or structured light and triangulation to obtain surface contour information for an object. In contour imaging, a pattern of lines or other features is projected toward the surface of an object from a given angle. The projected pattern on the surface is then viewed from another angle as a contour image, taking advantage of triangulation in order to analyze surface information and to characterize the surface contour based on the deformed appearance of the projected lines. Phase shifting, in which the projected line pattern is incrementally spatially shifted for obtaining additional measurements at higher resolution, helps to more accurately map the object's surface.

Surface contour imaging using structured light has been employed in a number of applications for determining the shape of solid, highly opaque objects. Contour imaging has also been used for characterizing the surface shape of portions of the anatomy and for obtaining detailed data about skin structure. However, a number of technical obstacles complicate effective use of contour projection imaging of the tooth. One particular challenge with dental surface imaging relates to tooth translucency. Translucent or semi-translucent materials in general are known to be particularly troublesome for patterned light imaging. Subsurface scattering in translucent structures can reduce the overall signal-to-noise (S/N) ratio and shift the light intensity, causing inaccurate height data. Another problem relates to high levels of reflection for various tooth surfaces. Highly reflective materials, particularly hollowed reflective structures, can effectively reduce the dynamic range of this type of imaging.

From an optical perspective, the structure of the tooth itself presents a number of additional challenges for structured light projection imaging. Teeth can be wet or dry at different times and along different surfaces and portions of surfaces. Tooth shape is often irregular, with sharp edges. As noted earlier, teeth interact with light in a complex manner. Light penetrating beneath the surface of the tooth tends to undergo significant scattering within the translucent tooth material. Moreover, reflection from opaque features beneath the tooth surface can also occur, adding noise that degrades the sensed signal and thus further complicates the task of tooth surface analysis. Not all light wavelengths can be detected with equal accuracy. Thus, a multi-spectral or multicolor approach can be less satisfactory in some cases.

Even where a coating or other type of surface conditioning of the tooth is used, however, results can be disappointing due to the pronounced contours of the tooth surface and inherent difficulties such as angular and space limitations. It can be difficult to provide sufficient amounts of light onto, and sense light reflected back from, all of the tooth surfaces. For example, different surfaces of the same tooth can be oriented at 90 degrees relative to each other, making it difficult to direct enough light for accurately imaging all parts of the tooth.

There have been a number of attempts to adapt structured light surface-profiling techniques to the problems of tooth structure imaging. For example, U.S. Pat. No. 5,372,502 entitled "Optical Probe and Method for the Three-Dimensional Surveying of Teeth" to Massen et al. describes the use of an LCD matrix to form patterns of stripes for projection onto the tooth surface. A similar approach is described in U.S. Patent Application Publication 2007/0086762 entitled "Front End for 3-D Imaging Camera" by O'Keefe et al. U.S. Pat. No. 7,312,924 entitled "Polarizing Multiplexer and Methods for Intra-Oral Scanning" to Trissel describes a method for profiling the tooth surface using triangularization and polarized light, but requiring application of a fluorescent coating for operation. Similarly, U.S. Pat. No. 6,885,464 entitled "3-D Camera for Recording Surface Structures, in Particular for Dental Purposes" to Pfeiffer et al. discloses a dental imaging apparatus using triangularization but also requiring the application of an opaque powder to the tooth surface for imaging. U.S. Pat. No. 6,885,464 to Pfeiffer et al. describes an intraoral camera that provides a group of light beams for imaging. Patent application WO 2011/145799 by Lim describes a 3-D scanner using scanned laser light. Patent application WO 2016/041147 by Liu describes a laser projection apparatus for contour imaging using a line laser.

Reference is hereby made to an article by Hiroshi Aoki entitled "Development of portable 3D optical measuring system using structured light projection method" in *Proceedings of SPIE*, vol. 9110 (2014) pp. 91100Q-1 to 91100Q-8; to an article by Tom Yoshizawa entitled "Compact Camera for Real-Time 3D Measurement" *10th IMEKO TC14 Symposium on Laser Metrology for Precision Measurement and Inspection in Industry* (September 2011) pp. 1-6; and to an article by Yasuhiro Takaki entitled "Micromirrors and 1D scanning produce an enlarged holographic color display" in *SPIE Newsroom* (2014) pp. 1-3.

Conventional methods for forming a pattern of lines include use of a 2-D array of micromirrors, such as those provided by a Digital Light Processor (DLP) from Texas Instruments, Inc., Dallas, Tex. Designs proposed for using these devices, however, are bulky and poorly suited for applications such as intraoral imaging. Alternate solutions using 2-D scanners have been proposed; however, these solutions do not allow imaging at the needed speed for intraoral applications.

Thus, it can be appreciated that there would be benefits to an optical apparatus for intraoral surface contour imaging that is highly compact, lightweight, and provides sufficient scan speed for practical use in intraoral imaging applications.

SUMMARY

It is an object of the present invention to advance the art of structured light generation for intraoral surface contour characterization.

Among advantages offered by the apparatus and method of the present invention are reduced size and weight of the projection apparatus.

These objects are given only by way of illustrative example, and such objects may be exemplary of one or more embodiments of the invention. Other desirable objectives and advantages inherently achieved by the disclosed methods may occur or become apparent to those skilled in the art. The invention is defined by the appended claims.

According to one aspect of the disclosure, there is provided an apparatus for intraoral imaging comprising:
  a) an intraoral camera that defines a field of view with a first dimension and a second dimension orthogonal to the first dimension;
  b) a projector having:
    (i) a laser diode energizable to emit a light beam;
    (ii) a collimator in the path of the emitted light beam;
    (iii) first beam-shaping optics disposed to shape the collimated beam in the second dimension to form a linear light pattern;
    (iv) focusing optics disposed to focus the shaped collimated beam at a focal plane;
    (v) a scanner that is disposed substantially at the focal plane and that is energizable to scan the formed linear light pattern along the second dimension to successive positions of the field of view;
  and
  c) a control logic processor that coordinates energizing the laser diode and scanner with image capture by the intraoral camera.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

DETAILED DESCRIPTION OF THE EMBODIMENTS

Figure 1:
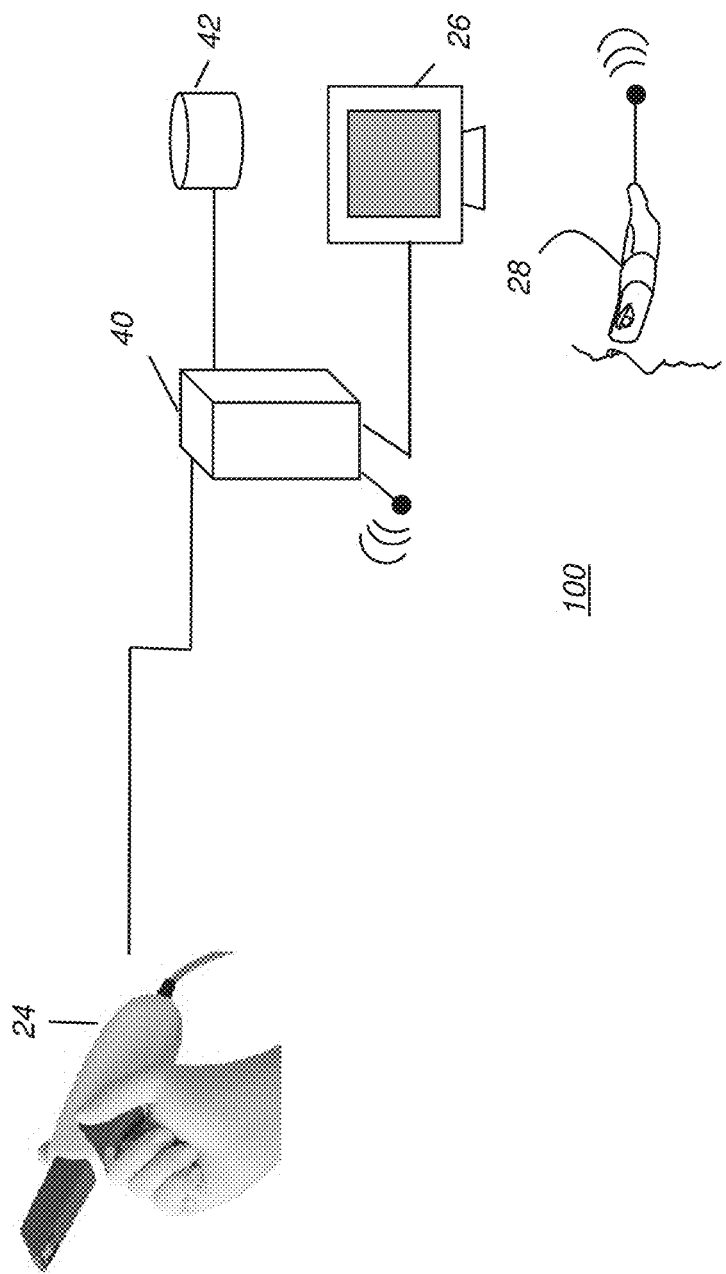
FIG. 1 shows an intraoral imaging apparatus for contour imaging of teeth.

The following is a detailed description of the preferred embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the term "structured light illumination" or "patterned illumination" are used to describe the type of projected illumination that is used for surface imaging or "contour" imaging that characterizes tooth shape. The structured light pattern itself can include, as patterned light features, one or more lines, circles, curves, or other geometric shapes that are distributed over the area that is illuminated and that have a predetermined spatial and temporal frequency. One exemplary type of structured light pattern that is widely used for contour imaging is a pattern of evenly spaced lines of light projected onto the surface of interest.

In the context of the present disclosure, the terms "structured light image" and "contour image" are considered to be equivalent and refer to the image that is captured during projection of the light pattern that is used for characterizing the tooth contour.

Two lines of light, portions of a line of light, or other features in a pattern of structured illumination can be considered to be substantially "dimensionally uniform" when their line width is the same over the length of the line to within no more than +/−15 percent. As is described in more detail subsequently, dimensional uniformity of the pattern of structured illumination is used to maintain a uniform spatial frequency.

In the context of the present disclosure, the term "optics" is used generally to refer to lenses and other refractive, diffractive, and reflective components used for shaping a light beam.

In the context of the present disclosure, the terms "viewer", "operator", and "user" are considered to be equivalent and refer to the viewing practitioner, technician, or other person who views and manipulates an image, such as a dental image, on a display monitor. An "operator instruction" or "viewer instruction" is obtained from explicit commands entered by the viewer, such as by clicking a button on a camera or by using a computer mouse or by touch screen or keyboard entry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

Apparatus and methods of the present invention address the need for a compact and lightweight system for intraoral structured light imaging by generating a line of light, suitably formed and sized to span the field of view, and scanning the generated line of light in one dimension along the tooth surface.

The schematic diagram of FIG. 1 shows an intraoral imaging system 100 having an intraoral scanning apparatus 24 for projecting structured light onto the surface of the tooth or other intraoral feature. Scanning apparatus 24 communicates, over a wired or wireless data communication channel, with a computer 40 that obtains the images from the projected structured light pattern. Computer 40 processes the images and provides output image data that can be stored as a data file and displayed on a display 26. Computer 40 can also store and retrieve image data with a memory 42 that is in signal communication with computer 40, such as in communication along a network. According to an alternate embodiment, a head-mounted display (HMD) 28 can be used for display of contour images obtained using system 100. HMD 28 can have an internal processor for generating image content or can be in signal communication with computer processor 40, such as through a wireless or wired link. Presentation on an HMD can be useful for functions such as surgical guidance, for example.

Figure 2A:
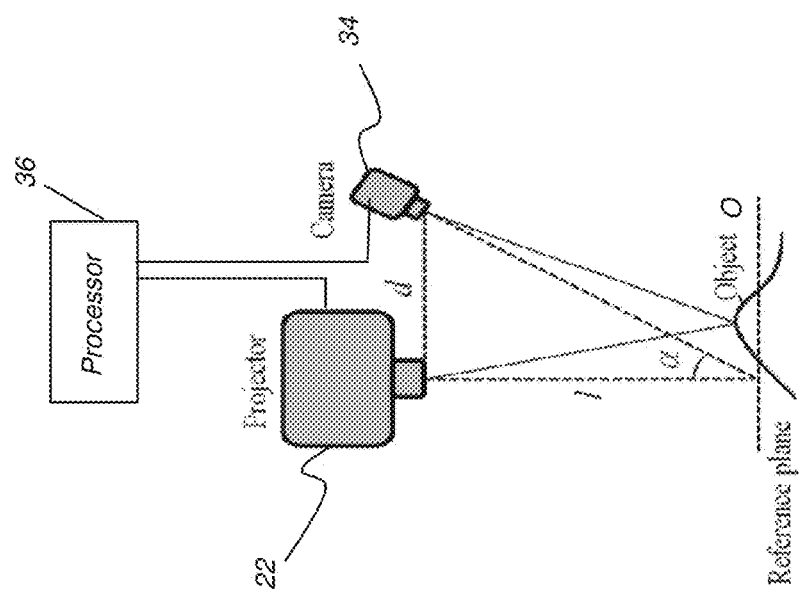
FIG. 2A is a schematic diagram that shows how triangularization is used to obtain surface contour data.
Figure 2B:
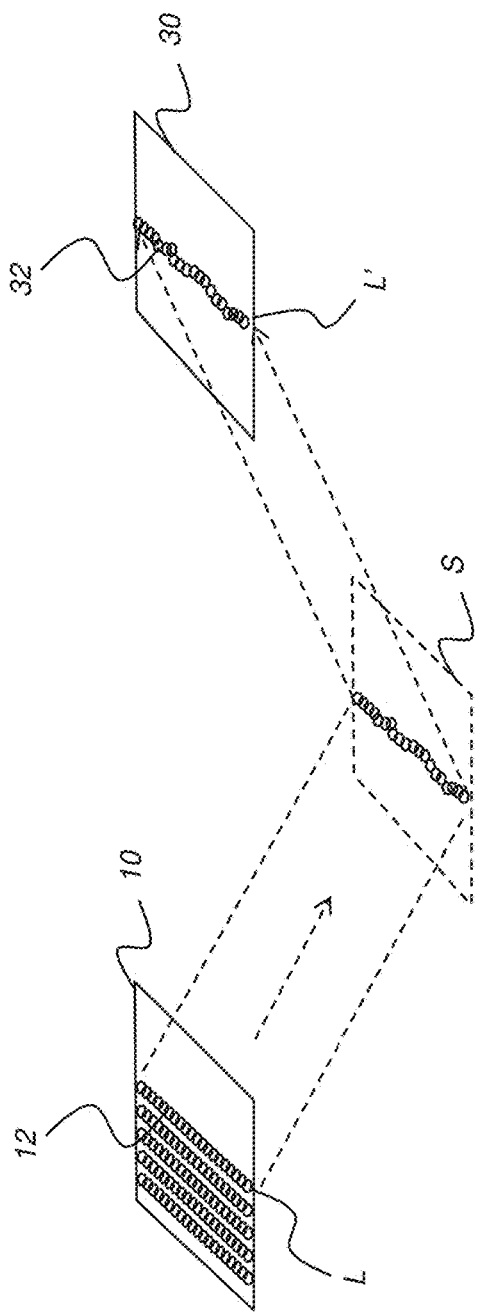
FIG. 2B is a schematic diagram that shows how patterned light is used for obtaining surface contour information.

The schematic diagrams of FIGS. 2A and 2B show how triangularization is used to obtain surface contour data. Provided within the chassis of scanning apparatus 24 shown in FIG. 1, a projector 22 and a camera 34, separated by a distance d, cooperate to scan the surface contour. According to an embodiment of the present disclosure, projector 22 directs successive lines of illumination over a distance 1 onto the object O at a reference plane. Camera 34, at the image plane, acquires image content corresponding to each projected line. Principal axes of projector 22 and camera 34 are offset from each other by an angle α. A control logic processor 36, such as a computer, dedicated microprocessor, or other logic processing device, synchronizes operation of projector 22 and camera 34 and obtains, stores, and processes or transmits the acquired image data from camera 34 in order to characterize the surface contour of object O.

The schematic diagram of FIG. 2B shows, for the example of a single line of light L that is projected from an illumination array 10, how patterned light is used for obtaining surface contour information when using a conventional array source. A mapping is obtained as illumination array 10 directs a pattern of light from projector 22 onto a surface S and a corresponding image of a line L' is formed on an imaging sensor array 30 of camera 34. Each pixel 32 on imaging sensor array 30 maps to a corresponding pixel 12 on illumination array 10 according to modulation by surface S. Shifts in pixel position, as represented in FIG. 2B, yield useful information about the contour of surface S. It can be appreciated that the basic pattern shown in FIG. 2B can be implemented in a number of ways, using a variety of illumination sources and sequences and using one or more different types of sensor arrays 30. Illumination array 10 can utilize any of a number of types of arrays used for light modulation, such as a liquid crystal array or digital micromirror array, such as that provided using the DLP device, as noted previously.

Using the concept described with reference to FIG. 2B, conventional structured light imaging apparatus used for contour imaging, such as apparatus using digital light processor (DLP) and similar modulation systems, form and project a 2-D image, multiple lines at a time, onto the target surface. Embodiments of the present disclosure do not use an array for line generation, but instead use an alternate approach that directs a single line of light toward the subject at a time.

By projecting and capturing images that show structured light patterns that duplicate the illumination arrangement shown in FIG. 2B multiple times, the image of the contour line on the camera simultaneously locates a number of surface points of the imaged object. This speeds the process of gathering many sample points, while the plane of light (and usually also the receiving camera) is laterally moved in order to "paint" some or all of the exterior surface of the object with the plane of light.

Multiple structured light patterns can be projected and analyzed together for a number of reasons, including to increase the density of lines for additional reconstructed points and to detect and/or correct incompatible line sequences. Use of multiple structured light patterns is described in commonly assigned U.S. Patent Application Publications No. US2013/0120532 and No. US2013/0120533, both entitled "3D INTRAORAL MEASUREMENTS USING OPTICAL MULTILINE METHOD" and incorporated herein in their entirety.

Figure 3:
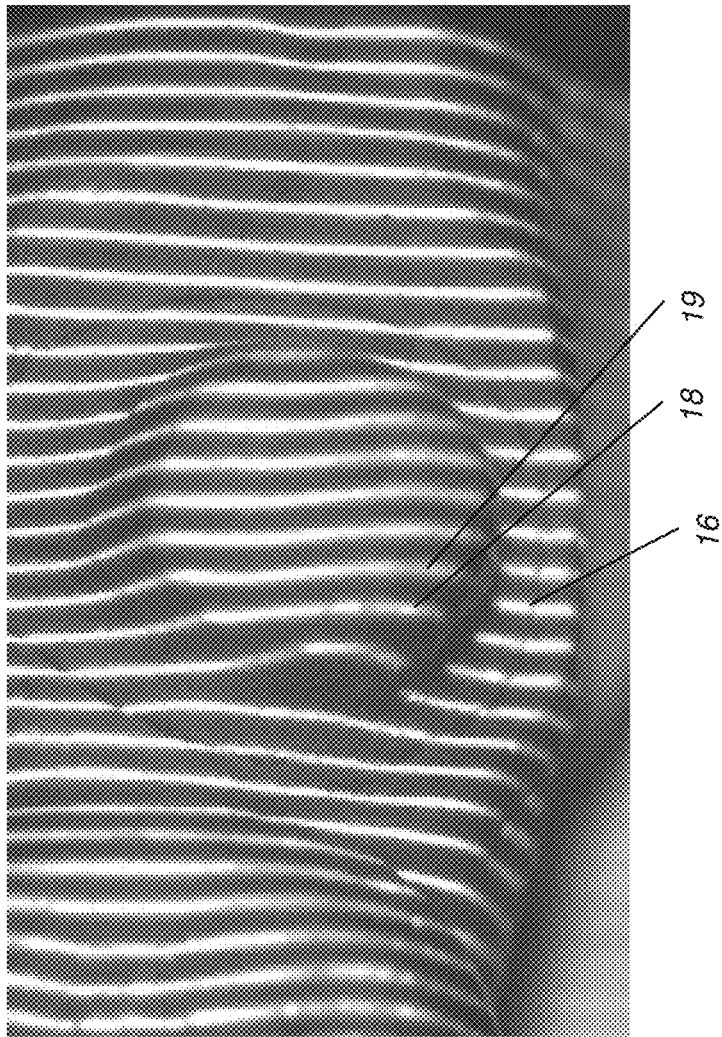
FIG. 3 is a diagram that shows surface imaging using a pattern with multiple lines of light.

FIG. 3 shows surface imaging using a pattern that has multiple lines of light. Incremental shifting of the line pattern and other techniques help to compensate for inaccuracies and confusion that can result from abrupt transitions along the surface, whereby it can be difficult to positively identify the segments that correspond to each projected line. In FIG. 3, for example, it can be difficult, over portions of the surface, to determine whether line segment 16 originates from the same line of illumination as line segment 18 or adjacent line segment 19.

An embodiment of the present disclosure addresses the need for accurate contour imaging of teeth and other intraoral features by providing a triangulation-based 3-D imaging apparatus having an illumination system that rapidly scans a line of light onto a subject surface at successive spatial increments using a highly compact and efficient arrangement of components. Unlike previously disclosed illumination solutions, the apparatus described herein employs one or more laser diodes for generating light, with supporting optics and with a reflective micro-electromechanical systems (MEMS) device for forming and scanning the patterned light over the tooth surface. The high speeds available from the light scanning apparatus allow this solution to be used with video 3D capture devices and other high speed image sensing components.

Figure 4:
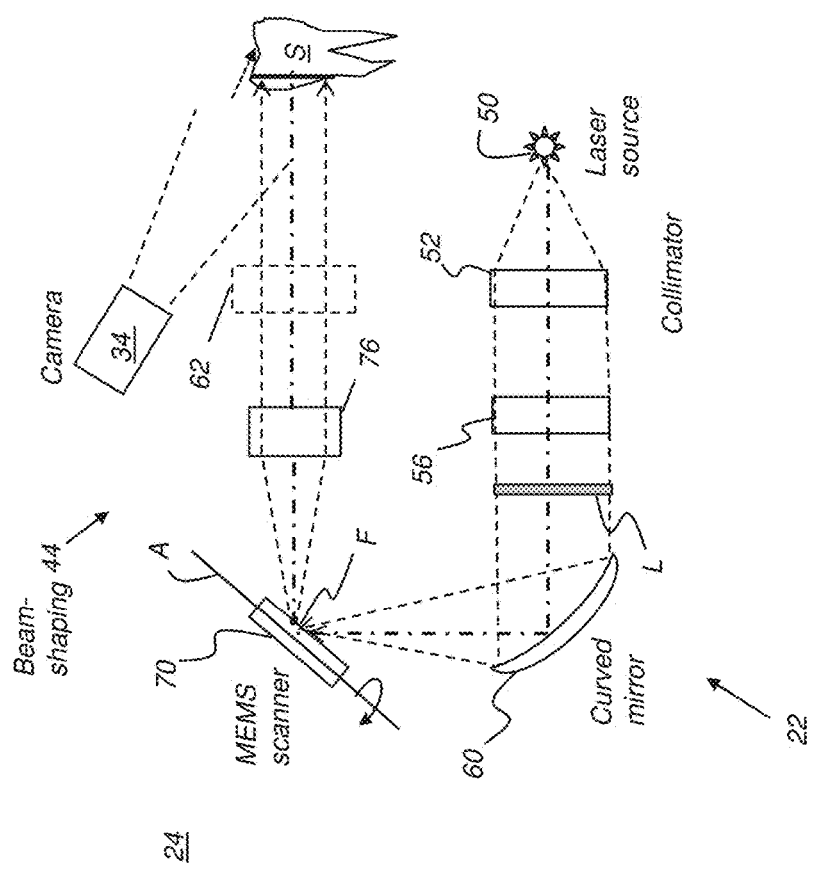
FIG. 4 is a schematic diagram that shows functional components of a scanning apparatus for surface contour characterization, according to an embodiment of the present disclosure.
Figure 5:
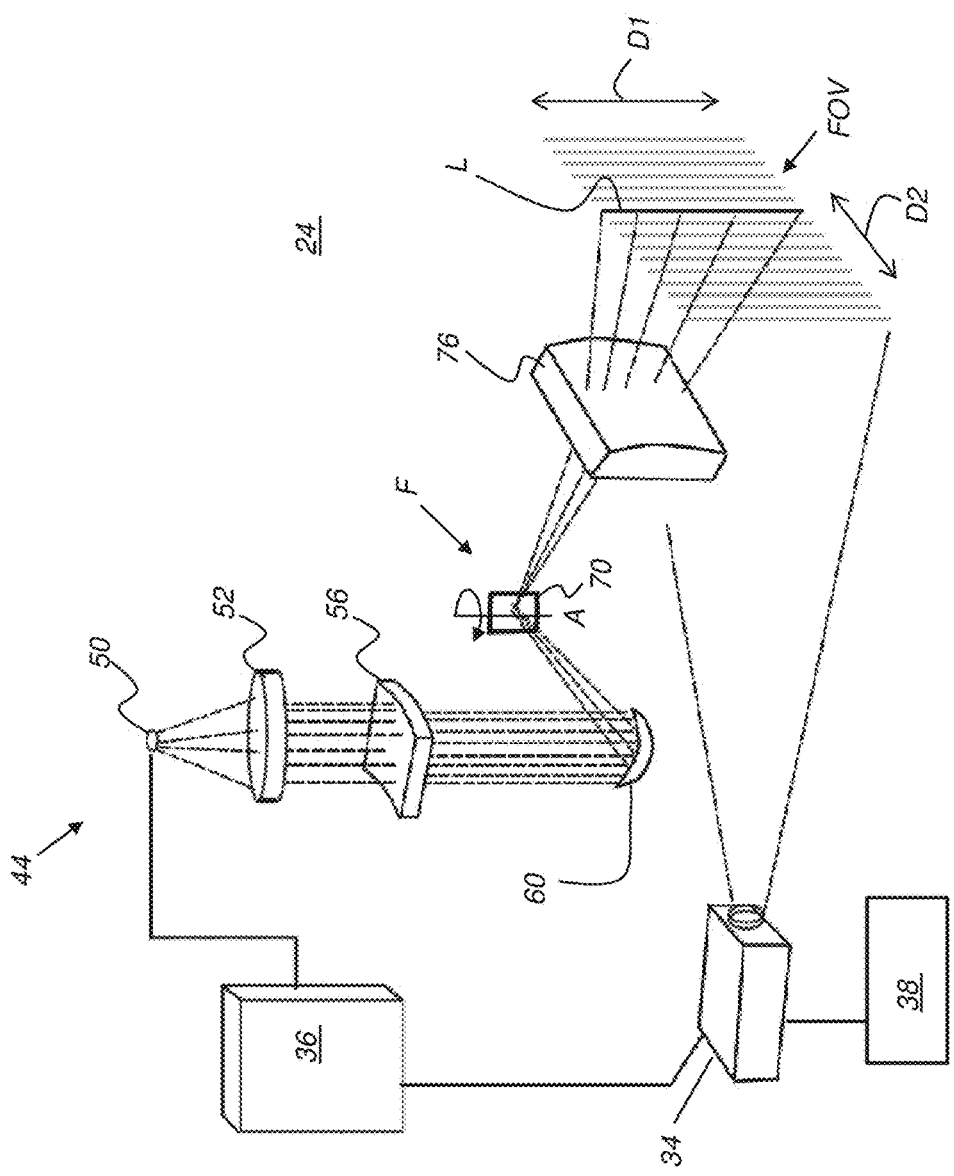
FIG. 5 is a perspective view of the scanning apparatus showing light handling.

The schematic diagrams of FIGS. 4 and 5 show functional components of scanning apparatus 24 for surface contour characterization, according to an embodiment of the present disclosure. In a projector 22, illumination from a laser source 50 is collimated by a lens 52 and directed beam-shaping optics 44 for forming the illumination with appropriate beam shaping. In the embodiment shown in FIG. 4, a first cylindrical lens 56 and a second cylindrical lens 76 provide beam-shaping as elements of beam-shaping optics 44. Cylindrical lens 56 provides refractive power only along one axis, forming a single line of illumination L. This line of light is directed by a curved mirror 60 to a reflective, single-axis MEMS scanner 70. Curved mirror 60 is a focusing optic that focuses the shaped beam from lens 56 at a focal plane F. A MEMS scanner 70 is disposed substantially at the focal plane F and is energizable to scan the shaped beam toward a second cylindrical lens 76 that shapes the line of light in the length direction in order to fit within the field of view (FOV) of camera 34 at sample surface S. By "substantially at the focal plane" is meant that the MEMS scanner 70 mirror is disposed within +/−15% of the focal distance of curved mirror 60 or other focusing optic. The beam width is at its narrowest point at the focal plane, allowing the MEMS scanner 70 mirror to have reduced dimensions when disposed as closely to focal plane F as possible; this positioning can translate to more compact component packaging and increased scanning speed. As the MEMS scanner 70 rotates about its axis A, it moves the line of light incrementally along the surface S to provide, over the scan interval, the structured light pattern such as that shown in FIG. 3.

Advantageously, the projector 22 arrangement of FIG. 4 allows for shaping of the structured light, so that various types of features can be used for the projected pattern. The light formed by beam-shaping optics 44 is a linear light pattern that can be provided as a set of individual points or can be modulated in some other way, provided the different structured light patterns can be suitably distinguished from each other on acquired images and used for surface contour characterization. The linear light pattern extends across one dimension of the camera FOV, with its length direction exceeding no more than about 10% of the corresponding FOV dimension.

With respect to the light path of FIG. 4, the two cylindrical lenses 56 and 76 provide refractive power along respectively orthogonal axes. Curved mirror 60 has optical power (alternately stated, has a focal point) and focuses the light received from lens 56 toward focal plane F. As noted previously, this focusing effect helps to reduce the beam size of light incident on the MEMS scanner 70 and its supporting optics. FIG. 4 shows focus of the light at or very near the scanner mirror. It should be noted that there can be conditions under which focus directly onto the MEMS mirror is useful; however, it may not be necessary to focus the output light directly on the scanner mirror surface, but rather near the mirror surface. At or near focus, the directed beam has reduced beam width dimensions.

FIG. 5 is a perspective view of the scanning apparatus showing light handling with beam-shaping optics 44. As described previously, each of cylindrical lenses 56 and 76 has power in a single direction. Beam shaping by cylindrical lens 56 helps to form line L having a line width, as measured on the subject surface S, of less than 100 microns, preferably of about 70 microns or less.

It should be noted that beam shaping by beam-shaping optics 44 can alternately be performed by any of a number of types of optical components. For example a GRIN (gradient refractive index) lens or a Powell lens could alternately be used for beam shaping, using methods familiar to those skilled in the optical arts. Gradient-index optics generate optical effects produced by a gradual variation of the refractive index of the lens. The Powell lens, formed as a round prism with a curved roof line, is a laser line generator familiar to those skilled in the laser art, stretching a narrow laser beam into a uniformly illuminated straight line.

It can be appreciated that other arrangements of the optical path beam-shaping can be used. This can include positioning of the focusing optics and the MEMS scanning mirror after the two-directional beam shaping optics represented by lenses 56 and 76. Curved mirror 60 offers the advantage of providing focus as well as folding the optical path; alternately, a lens could be used for providing focus.

The optical path and cylindrical lens 76 are designed to dimension the length of the line L projected at each MEMS scanner position so that it is suited to the camera 34 FOV without wasting light that could otherwise be randomly reflected from other surfaces outside the FOV and would act as noise. According to an embodiment, scanning apparatus 24 directs more than 90 percent of the scanned light within the FOV defined by camera 34. The light can be clipped through an optional aperture 62 as shown in FIG. 4 or using some other method in order to trim the length of the linear light beam to a dimension D1. The aperture 62 can be fixed or can allow adjustment to compensate for different FOV dimensions. An operator control can be used to enter instructions defining one or both dimensions of the FOV for an imaging apparatus or for a particular imaging session, such as to limit image acquisition to a limited area of the mouth, for example. Instructions for FOV adjustment can be entered on an operator interface that cooperates with display 26 (FIG. 1) or using a dial or other mechanical adjustment device provided on scanning apparatus 24. Beam-shaping optics can be designed to provide the needed depth of field for intraoral use.

Laser source 50 can be monochromatic, with a single laser source, or may have alternating or combined spectral content, provided along the same optical path from multiple lasers, with light of different wavelength bands combined using dichroic beamsplitters or other means.

Rotation of MEMS scanner 70 can be coordinated with generation of light by laser source 50 and image capture by camera 34 in order to provide the needed patterned image content for surface contour characterization. According to an embodiment, the camera 34 exposure time corresponds to the timing of a full scan across the FOV in a second dimension D2, shown in FIG. 5, so that the exposure time and scan cycle are equal to within 8%. An optional operator control 38 can be provided to allow adjustment of one or both dimensions D1, D2 of the camera 34 FOV and, at the same time, to adjust the scan dimension D2 and line length dimension D1 accordingly.

Figure 6:
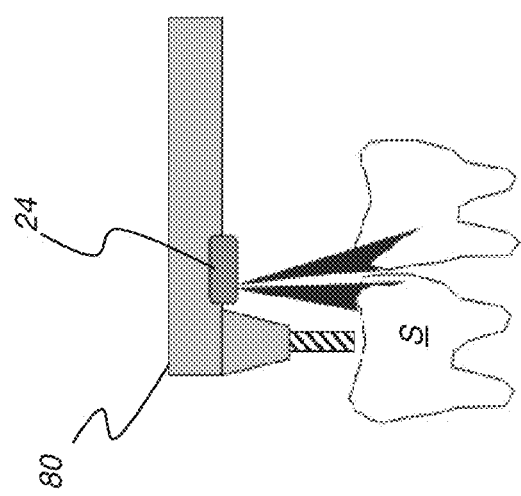
FIG. 6 is a schematic diagram that shows an intraoral instrument that incorporates the scanning apparatus in a stem or handle.

According to an alternate embodiment of the present disclosure, the projection apparatus 22 and camera 34 of scanning apparatus 24, due to their small relative size, can be integrated into any of a number of types of intraoral device. The schematic diagram of FIG. 6 shows an intraoral instrument 80 such as a drill that incorporates scanning apparatus 24 in a stem or handle, enabling the practitioner to have the advantages of close-up visibility of the surface S being treated. This can allow close inspection and surgical guidance functions, for example. According to an embodiment of the present disclosure, the resulting surface contour can be displayed in an HMD display 28, as shown in FIG. 1.

Figure 7:
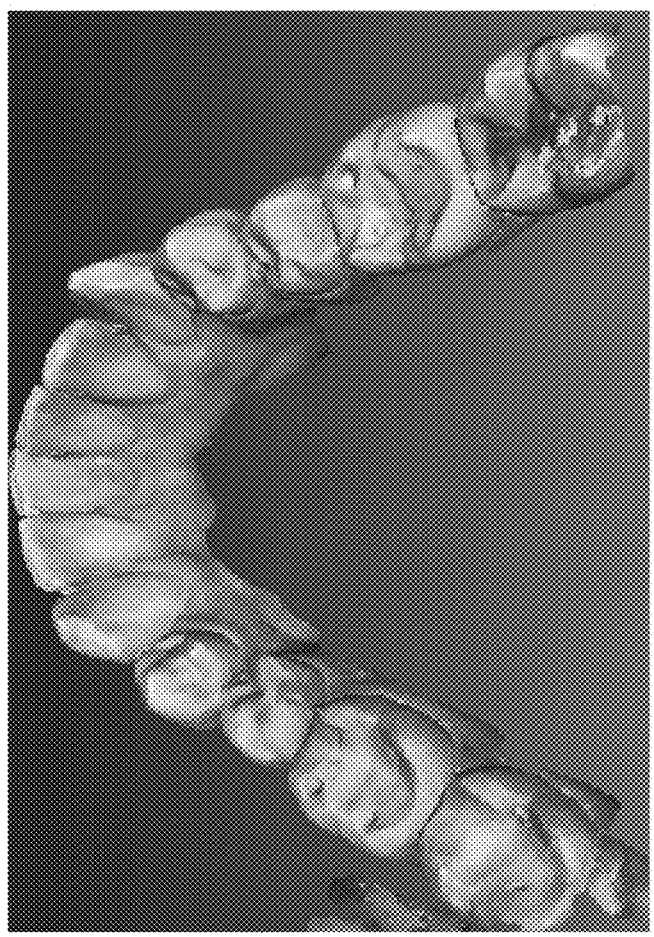
FIG. 7 shows a portion of a contour image formed using pattern of parallel lines of light.

Once the needed images of the scan pattern are acquired, the contour image can be formed, using computation techniques well known to those skilled in the surface imaging arts. By way of example, FIG. 7 shows a portion of a contour image 92 formed using pattern of parallel lines of light.

Advantageously, the apparatus and method of the present invention provide an intraoral imaging system for 3-D imaging of teeth and other dental features without requiring the use of a special powder or application of some other temporary coating for the tooth surface. The system offers high resolution, in the 25-50 μm range in one embodiment. The working distance of the scanning apparatus 24 (FIGS. 4, 5) can be less than 20 mm, allowing intraoral use. The speed of structured light generation and pattern projection can support video-captures of contour images at high frame rates, such as 240 frames per second (fps) or faster.

Consistent with an embodiment of the present invention, a computer program utilizes stored instructions that perform on image data that is accessed from an electronic memory. As can be appreciated by those skilled in the image processing arts, a computer program for operating the imaging system in an embodiment of the present invention can be utilized by a suitable, general-purpose computer system, such as a personal computer or workstation. However, many other types of computer systems can be used to execute the computer program of the present invention, including an arrangement of networked processors, for example.

The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. The presently disclosed embodiments are therefore considered in all respects to be illustrative and not restrictive. Other embodiments of the invention will be apparent to those skilled in the art from consideration of the specification and practice of the invention disclosed herein. The scope of the invention is indicated by the appended claims, and all changes that come within the meaning and range of equivalents thereof are intended to be embraced therein.

What is claimed is:

1. An apparatus for intraoral imaging comprising:
   a) an intraoral camera that defines a field of view with a first dimension and a second dimension orthogonal to the first dimension;
   b) a projector having:
      (i) a laser diode energizable to emit a light beam;
      (ii) a collimator in the path of the emitted light beam;
      (iii) first beam-shaping optics disposed to shape the collimated beam in the second dimension to form a linear light pattern;
      (iv) focusing optics disposed to focus the shaped collimated beam at a focal plane;
      (v) a scanner that is disposed substantially at the focal plane and that is energizable to scan the formed linear light pattern along the second dimension to successive positions of the field of view; and
   c) a control logic processor that coordinates energizing the laser diode and scanner with image capture by the intraoral camera, wherein a line width of the linear light pattern in the second dimension is less than 100 microns.

2. The apparatus of claim 1 wherein the first beam-shaping optics comprise at least a first cylindrical lens.

3. The apparatus of claim 1 wherein the focusing optics comprise a curved mirror or a lens.

4. The apparatus of claim 1 wherein the first beam-shaping optics comprise a Powell lens.

5. The apparatus of claim 1 wherein the first beam-shaping optics comprise a GRIN lens.

6. The apparatus of claim 1 further comprising second beam-shaping optics disposed to shape the formed linear light pattern in the first dimension to extend fully across the field of view with respect to the first dimension.

7. The apparatus of claim 6 wherein the second beam-shaping optics comprise a second cylindrical lens.

8. The apparatus of claim 1 wherein the formed linear light pattern has a length that is no more than 10% longer than the first dimension, and wherein the camera is a video camera.

9. The apparatus of claim 1 wherein the camera exposure time corresponds to the timing of a full scan across the FOV in the second dimension.

10. The apparatus of claim 1 further comprising an operator control for adjusting one or both of the line length in the first dimension and scan length in a second dimension of the projected linear light pattern.

11. The apparatus of claim 1 wherein a line width of the linear light pattern in the second dimension is less than 70 microns.

12. An apparatus for intraoral imaging comprising:
   a) an intraoral camera that defines a field of view with a first dimension and a second dimension orthogonal to the first dimension;

b) a projector having:
  (i) a laser diode energizable to emit a light beam;
  (ii) a collimator in the path of the emitted light beam;
  (iii) a first cylindrical lens in the path of the light beam from the collimator to shape the collimated light beam in the second dimension to form a linear light pattern;
  (iv) a curved mirror in the path of the light beam from the collimator to focus the formed linear light pattern at a focal plane;
  (v) a scanner that is disposed substantially at the focal plane and that is energizable to scan the formed linear light pattern along the second dimension to successive positions of the field of view;
  (vi) a second cylindrical lens to shape the formed linear light pattern in the first dimension to extend fully across the field of view; and
c) a control logic processor that coordinates energizing the laser diode and scanner with image capture by the intraoral camera.

13. The apparatus of claim 12 wherein the shaped linear light pattern has a length that is no more than 10% longer than the first dimension.

14. The apparatus of claim 12 wherein the camera exposure time corresponds to the timing of a full scan across the field of view in the second dimension, wherein a line width of the linear light pattern is less than 70 microns.

15. The apparatus of claim 12 further comprising an operator control for adjusting one or both of the line length in the first dimension and scan length in a second dimension of the projected linear light pattern.

16. The apparatus of claim 12 wherein a line width of the linear light pattern is less than 100 microns.

17. The apparatus of claim 12 further comprising an adjustable aperture for adjusting the height of the linear light pattern.

18. A method for intraoral imaging, the method executed at least in part by a computer and comprising:
  a) defining a field of view of an intraoral camera having a first dimension and a second dimension orthogonal to the first dimension;
  b) energizing a laser diode energizable to emit a light beam;
  c) collimating the emitted light beam;
  d) shaping the collimated light beam in the second dimension to form a linear light pattern;
  e) focusing the linear light pattern;
  f) scanning the focused light pattern along the second dimension to successive positions of the field of view;
  g) recording one or more images of the scanned linear light pattern on the intraoral camera; and
  h) generating and displaying a contour image formed according to the recorded one or more images, wherein a line width of the linear light pattern in the second dimension is less than 100 microns.

19. The method of claim 18 wherein shaping the collimated light beam comprises directing the collimated light beam to a first cylindrical lens, further comprising shaping the formed linear light pattern in the first dimension to extend fully across the defined field of view, with respect to the first dimension of the intraoral camera, and wherein shaping the formed linear light pattern further comprises directing the formed linear light pattern to a second cylindrical lens.

20. The method of claim 18 wherein a line width of the linear light pattern is less than 70 microns.

* * * * *